US012167882B2

(12) United States Patent
Seith et al.

(10) Patent No.: US 12,167,882 B2
(45) Date of Patent: Dec. 17, 2024

(54) UTILIZATION OF SYNERGY EMR AND EML TO CREATE A COXMAZE3 BOX LESION WITH RADIO FREQUENCY

(71) Applicant: AtriCure, Inc., Mason, OH (US)

(72) Inventors: Douglas J. Seith, Mason, OH (US); Richard Hufstetler, Mason, OH (US); John T. Wesley, Mason, OH (US)

(73) Assignee: AtriCure, Inc., Mason, OH (US)

( * ) Notice: Subject to any disclaimer, the term of this patent is extended or adjusted under 35 U.S.C. 154(b) by 492 days.

(21) Appl. No.: 17/478,779

(22) Filed: Sep. 17, 2021

(65) Prior Publication Data

US 2023/0087254 A1    Mar. 23, 2023

(51) Int. Cl.
*A61B 18/00* (2006.01)
*A61B 18/08* (2006.01)
*A61B 18/14* (2006.01)
*A61B 17/00* (2006.01)

(52) U.S. Cl.
CPC ........ *A61B 18/082* (2013.01); *A61B 18/1442* (2013.01); *A61B 18/1492* (2013.01); *A61B 2017/00243* (2013.01); *A61B 2018/00351* (2013.01); *A61B 2018/00363* (2013.01); *A61B 2018/00577* (2013.01)

(58) Field of Classification Search
CPC .............. A61B 2018/00351–00375; A61B 2018/00577; A61B 2018/145
See application file for complete search history.

(56) References Cited

U.S. PATENT DOCUMENTS

| | | | |
|---|---|---|---|
| 7,001,415 B2 | 2/2006 | Hooven | |
| 8,029,528 B2 | 10/2011 | Miller et al. | |
| 8,096,990 B2 | 1/2012 | Swanson et al. | |
| 10,342,610 B2 | 7/2019 | Fleischman et al. | |
| 10,398,495 B2 | 9/2019 | Morejohn et al. | |
| 2006/0235372 A1* | 10/2006 | Ward | A61B 18/1492 606/13 |
| 2007/0208336 A1* | 9/2007 | Kim | A61B 18/1492 606/41 |

(Continued)

OTHER PUBLICATIONS

James L. Cox, The Standard Maze-III Procedure, Operative Techniques in Thoracic and Cardiovascular Surgery, vol. 5, Issue 1, 2000, pp. 2-22, ISSN 1522-2942, (https://www.sciencedirect.com/science/article/pii/S152229420080015X). (Year: 2000).*

(Continued)

*Primary Examiner* — Jaymi E Della
(74) *Attorney, Agent, or Firm* — Levine Bagade Han LLP

(57) ABSTRACT

Various methods of treating a heart of a patient having a cardiac arrhythmia are disclosed. The method can comprise dissecting tissue at an inferior aspect of a right inferior pulmonary vein of the patient to create an oblique sinus defect, dissecting tissue to open a space between a superior vena cava and a left atrium, and dissecting tissue to open a space across a transverse sinus between a pulmonary artery and a roof of the left atrium. The method can further comprise passing a catheter through an oblique sinus defect underneath the heart and beyond a left ventricle and passing a first flexible guiding device across the transverse sinus and under the superior vena cava and the pulmonary artery.

15 Claims, 15 Drawing Sheets

(56) References Cited

U.S. PATENT DOCUMENTS

| | | | | |
|---|---|---|---|---|
| 2012/0310237 A1* | 12/2012 | Swanson | ............... | A61B 18/08 |
| | | | | 606/41 |
| 2013/0282005 A1* | 10/2013 | Koch | .................... | A61B 90/36 |
| | | | | 606/41 |
| 2014/0316385 A1* | 10/2014 | Longoria | ........... | A61B 18/1445 |
| | | | | 606/41 |

OTHER PUBLICATIONS

Nguyen, et al., Transaortic Septal Myectomy for Obstructive Hypertrophic Cardiomyopathy, Operative Techniques in Thoracic and Cardiovascular Surgery, vol. 22, Is. 4, 2017, pp. 200-215 (https://www.sciencedirect.com/science/article/pii/S1522294218300576). (Year: 2017).*

Robertson JO, Saint LL, Leidenfrost JE, Damiano RJ Jr. Illustrated techniques for performing the Cox-Maze IV procedure through a right mini-thoracotomy. Ann Cardiothorac Surg. Jan. 2014;3(1):105-16. doi: 10.3978/j.issn.2225-319X.2013.12.11. PMID: 24516807; PMCID: PMC3904342. (Year: 2014).*

Screen captures from YouTube video clip entitled "How to shorten a coronoary guide catheter," uploaded on Sep. 26, 2012 by user Manos Brilakis. Retrieved from Internet: <https://web.archive.org/web/20170329012713/https://www.youtube.com/watch?v=hrbU6w2S0Y4>. (Year: 2017).*

* cited by examiner

UTILIZATION OF SYNERGY EMR AND EML TO CREATE A COXMAZE3 BOX LESION WITH RADIO FREQUENCY

TECHNICAL FIELD

This application relates to a procedure for ablating a back wall of the heart in a novel manner, such as for atrial fibrillation that interrupts pathways for reentry circuits.

BACKGROUND OF THE INVENTION

Surgical methods maze-like procedures are introduced for atrial fibrillation by interrupting pathways for re-entry circuits, such as the "maze procedure" or "cox-maze procedure." Such procedure can use a pattern of incisions to anatomically create a convoluted path, or maze, for electrical propagation in the left atrium and the right atrium. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

Maze-like procedures have also been developed utilizing radio frequency (RF) energy which can form lesions on the endocardium to effectively create a maze for electrical conduction in a predetermined path. Typically, the lesions are formed by ablating tissue with an electrode, such as carried by a catheter or via open heart surgery. Electromagnetic RF energy applied by the electrode heats, and eventually kills (i.e., "ablates"), the tissue to form a lesion. During the ablation of soft tissue (i.e., tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

The maze procedure is further described, for example, in U.S. Pat. No. 8,096,990, which is hereby incorporated by reference in its entirety as if fully set forth below in its entirety and for all applicable purposes.

The following procedures/methods can be best performed while the heart is on bypass and or arrested and as empty as possible. It can also be performed with the surgeon in their traditional position on the right side of the patient.

SUMMARY OF INVENTION

In one variation, a method of treating a heart of a patient having a cardiac arrhythmia is disclosed. The method can comprise dissecting tissue at an inferior aspect of a right inferior pulmonary vein of the patient to create an oblique sinus defect, dissecting tissue to open a space between a superior vena cava and a left atrium, and dissecting tissue to open a space across a transverse sinus between a pulmonary artery and a roof of the left atrium. The method can further comprise passing a catheter through an oblique sinus defect underneath the heart and beyond a left ventricle and passing a first flexible guiding device across the transverse sinus and under the superior vena cava and the pulmonary artery.

The method can further comprise reducing a length of an open end of the catheter and grasping the open end of the catheter with a first ablation device. Reducing the length of the open end of the catheter can comprise reducing the length by about 50% and can comprise cutting the open end of the catheter. The first ablation device can comprise a proximal jaw and a distal jaw configured to secure the open end. The method can further comprise advancing the first ablation device in a rotating counterclockwise motion such that the distal jaw of the first ablation device advances across the transverse sinus and the proximal jaw of the first ablation device is guided across a floor of an oblique sinus. The method can further comprise marking a position on an atrium proximal to a distal tip of the proximal jaw and activating the first ablation device to create a first ablation on the heart.

The method can further comprise placing the open end of the catheter onto the proximal jaw of the first ablation device. The method can further comprise removing slack from the catheter and the first ablation device. The method can further comprise advancing the first ablation device until the proximal jaw reaches up to the left inferior pulmonary vein. The method can further comprise closing the proximal and distal jaws of the first ablation device. The method can further comprise creating a marked position on the atrium proximal to a distal tip of the proximal jaw. The method can further comprise opening and extracting the first ablation device while the catheter and the first flexible guiding device are maintained proximal to the transverse sinus.

The method can further comprise connecting a distal end of a second flexible guiding device to a distal end of the first flexible guiding device and retracting the first flexible guiding device. Retracting the first flexible guiding device can cause the second flexible guiding device to be pulled through the transverse sinus and beyond the superior vena cava. The method can further comprise detaching the first flexible guiding device from the second flexible guiding device. The method can further comprise attaching the second flexible guiding device to a second ablation device after detaching the first flexible guiding device from the second flexible guiding device. The method can further comprise advancing the second ablation device while applying traction to the second flexible guiding device such that a distal jaw of the second ablation device extends across the transverse sinus until a proximal jaw of the second ablation device crosses the marked position on the atrium. Advancing the second ablation device can comprise a clockwise rotation and a downward advancement of the proximal and distal jaws of the second ablation device.

A second ablation can be performed with the second ablation device. The method can further comprise opening and extracting the second ablation device in response to an ablation line from the first ablation device crossing an ablation line from the second ablation device. The method can further comprise repeating operations related to the second ablation device in response to the ablation line from the first ablation device not crossing the ablation line from the second ablation device. The first ablation device can be advanced no further than an inferomedial aspect of a left inferior pulmonary vein. The method can further comprise retracting the left ventricle with a sponge.

DETAILED DESCRIPTION OF THE INVENTION

Embodiments of the present invention encompass systems and methods that involve a treatment system having a disposable dedicated bipolar clamp. In some cases, a bipolar clamp device can include cooled RF technology. Optionally, treatment devices can include a flexible serpentine plate electrode. Treatment devices can be adjustable for ease of use by the surgeon in any of a variety of configurations, including a right-hand configuration, a left-hand configuration, a jaws up configuration, and a jaws down configuration. The treatment device can adopt such configurations as the surgeon adjustably flips or rotates the jaws through various degrees of angular rotation. In some cases, a treatment device includes a symmetric, unified release trigger.

FIGS. 1A-1K show one variation of a method of treating a heart 100 of a patient having a cardiac arrhythmia. The methods as described herein can be best performed when the heart is on bypass and/or arrested and as empty as possible. In one variation, the operator can be positioned on the right side of the patient.

Figure 1A:
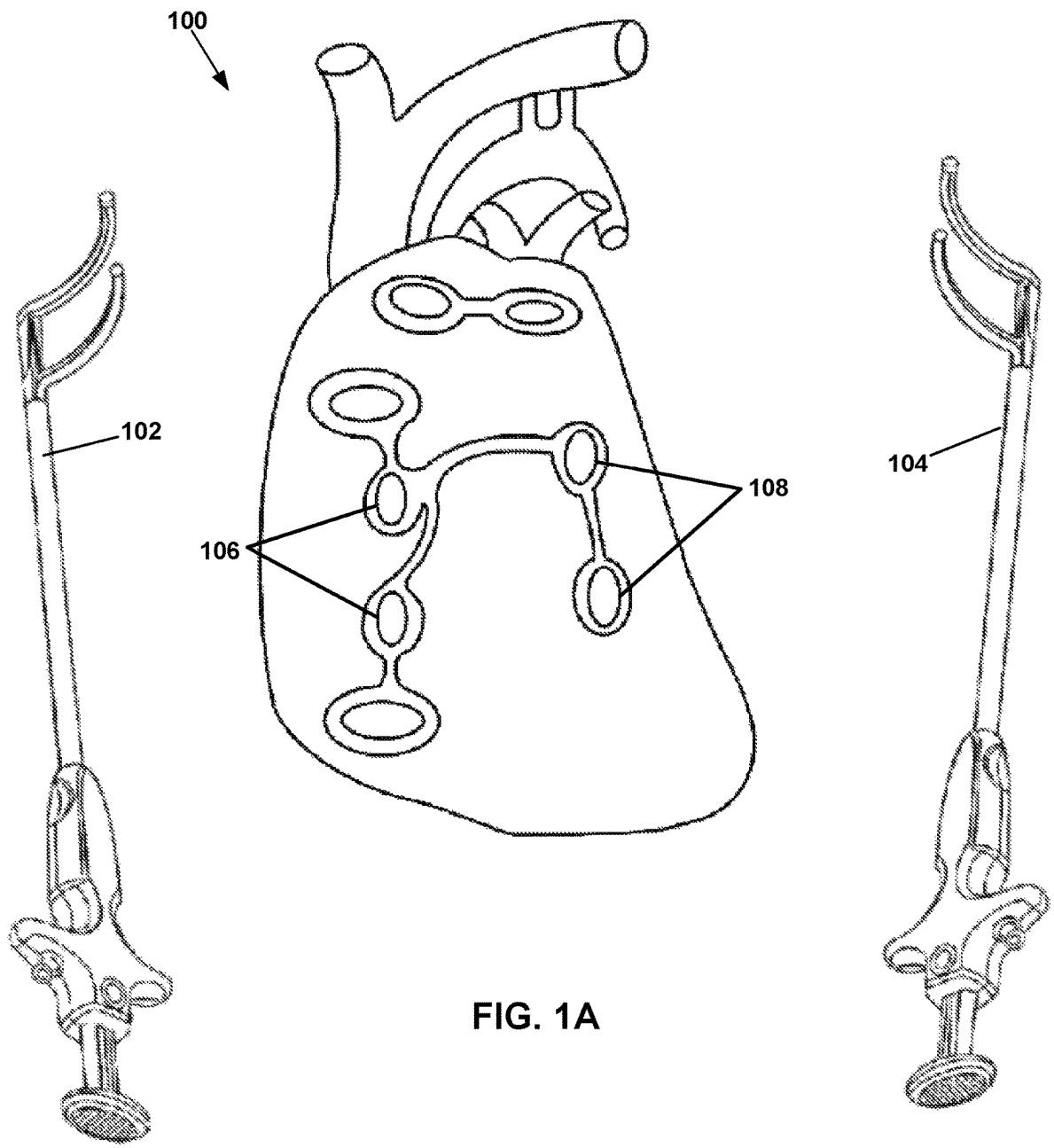
FIG. 1A illustrates an anterior view of a heart and clamps with jaws of right and left curvatures.
Figure 2A:
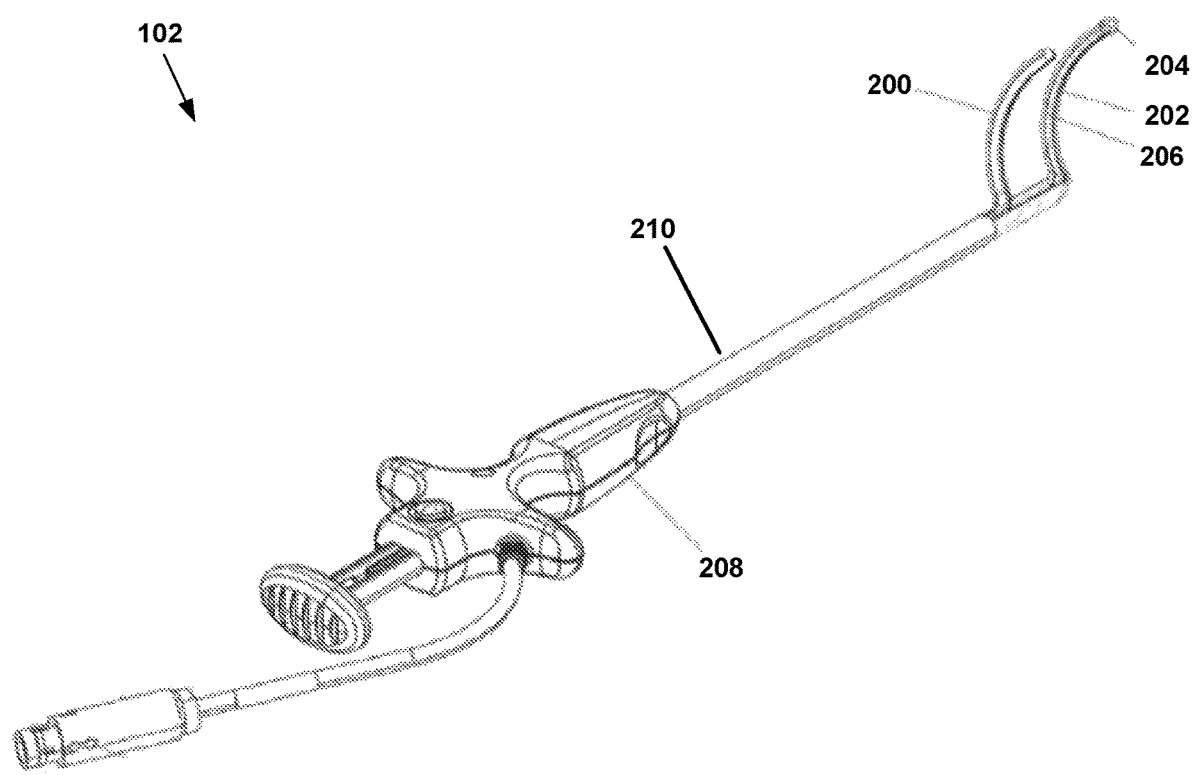
FIG. 2A illustrates an example of an ablation device for use with the methods described herein.

FIG. 1A illustrates an anterior view of a heart 100 and clamps with jaws of right and left curvatures. Right pulmonary veins 106 and left pulmonary veins 108 are also shown for orientation purposes. First ablation device 102 can have right-curved jaws configured for maneuverability within the anatomy. Second ablation device 104 can have left-curved jaws also configured for maneuverability within the anatomy. The first and second ablation devices can have a clamp configured to compress right pulmonary veins 106 and left pulmonary veins 108. The first and second ablation devices will be further described herein, as seen in FIG. 2A.

Figure 1B:
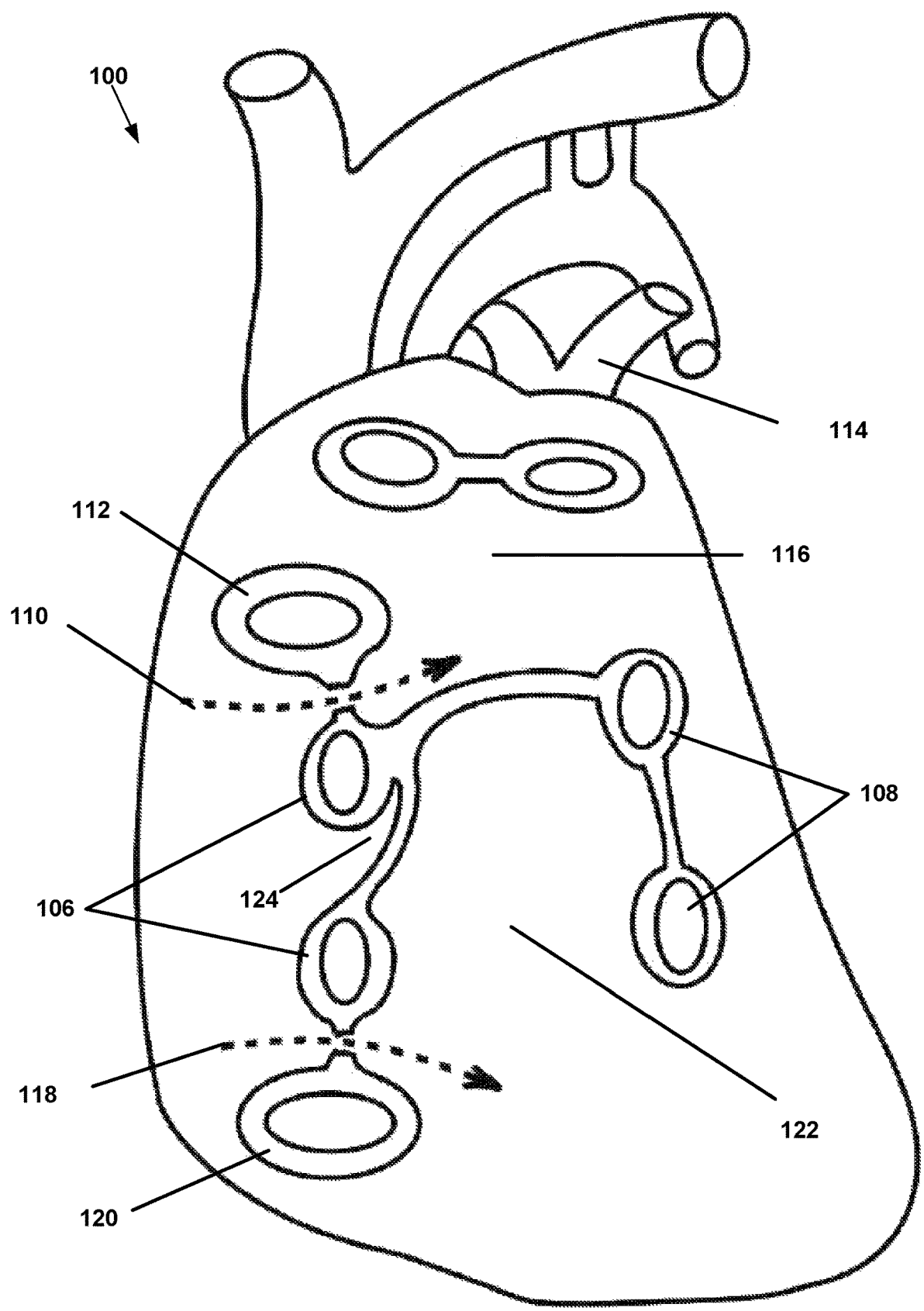
FIG. 1B illustrates an anterior view of the heart with dissections created within.

FIG. 1B illustrates an anterior view of the heart with dissections created within. First, the method can comprise blunt dissection of tissue to open a space between the superior vena cava 112 and the right superior pulmonary vein 106, shown by first dissection arrow 110. The dissection can open a space across the transverse sinus 116 between the main pulmonary artery 114 and the roof of the left atrium. Next, the method can comprise blunt dissection between the right inferior pulmonary vein 106 and inferior vena cava 120 towards the oblique sinus 122, shown via second dissection arrow 118. This can create an oblique sinus 122 defect. Dissections can force the tissue to be completely open and can be made via fingers of the operator. Both first and second dissections 110 and 118 can create tunnels into the transverse sinus and oblique sinus respectively. The tunnels can provide passage of devices from the right side of the heart to the left side of the heart. Tissue near the right pulmonary vein recess 124 may stay intact during dissections.

Figure 1C:
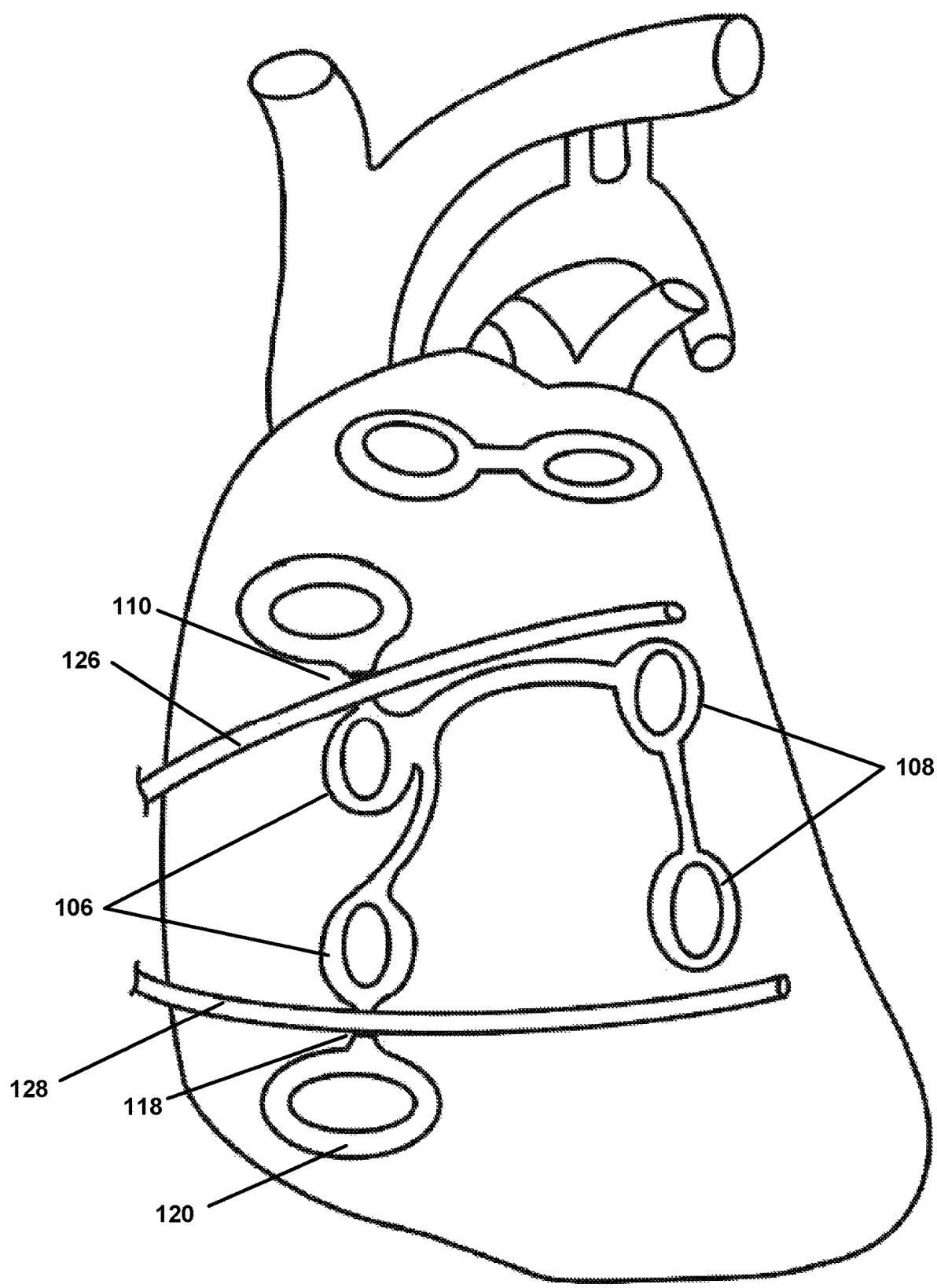
FIG. 1C illustrates an anterior view of the heart having a flexible guiding device and a catheter passed within.
Figure 2B:
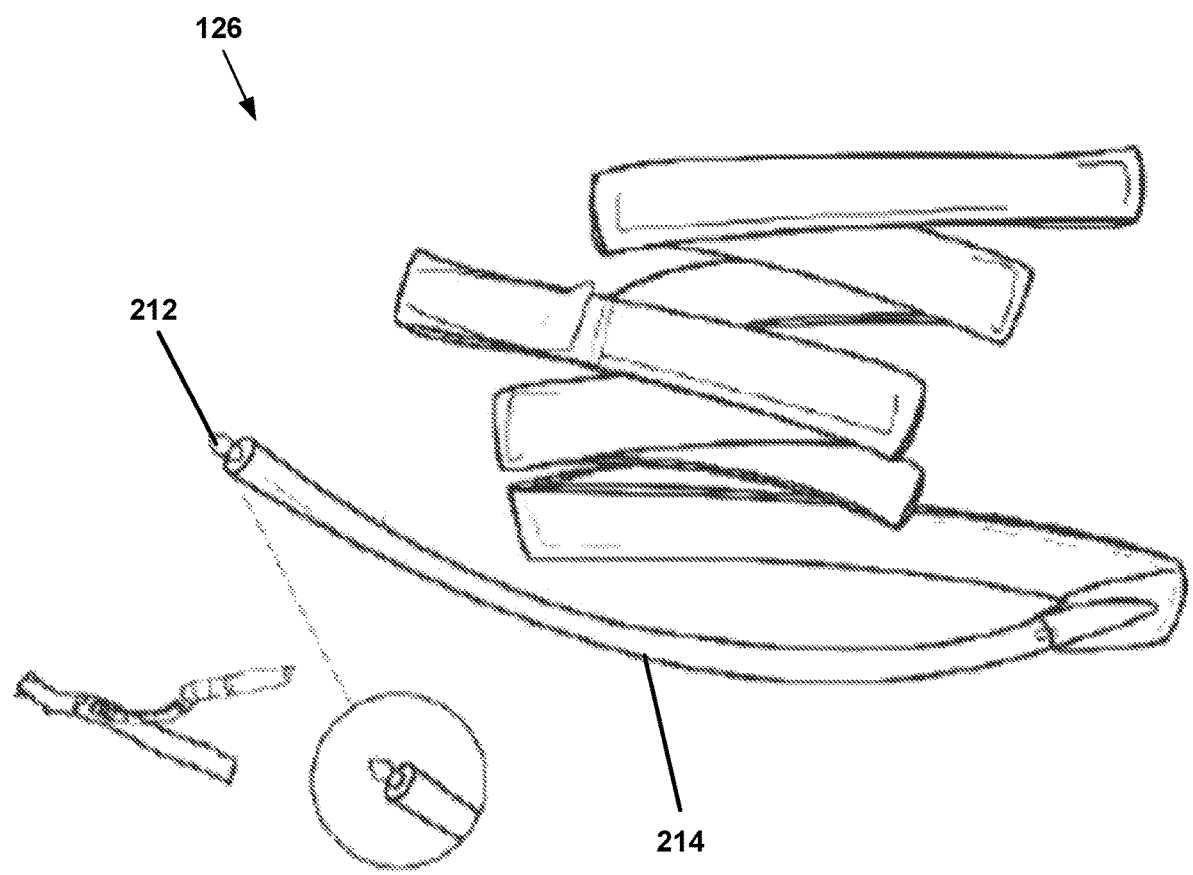
FIG. 2B illustrates an example of a flexible guiding device for use with the methods described herein.

FIG. 1C illustrates an anterior view of the heart having a flexible guiding device 126 and a first catheter 128 passed within. First, a first flexible guiding device 126 can be opened in a sterile field. The first flexible guiding device 126 can be designed to facilitate the guidance of a surgical instrument through soft tissue during a surgical procedure. The first flexible guiding device 126 can attach to a surgical instrument by either permanently or detachably attaching to the surgical instrument. In some variations, the first flexible guiding device 126 can be a Glidepath™ Tape Instrument Guide, for example, as shown in FIG. 2B. The first flexible guiding device 126 can be passed through the first dissection 110 across the transverse sinus 116 and under the superior vena cava 112 and the pulmonary artery using standard clamping techniques until the first flexible guiding device 126 can be easily grasped and controlled from the left side of the table.

Additionally, a first catheter 128 having a size of about 20 French (Fr) can be passed through the second dissection 118 and into the oblique sinus 122 defect, underneath the heart 100 and beyond the left ventricle so that it is visible and easy to grasp and control from the left side of a table. Once delivered, the method can further comprise reducing (e.g., by cutting) a length of an open or flanged end of the first catheter 128 by approximately 50%.

Figure 1D:
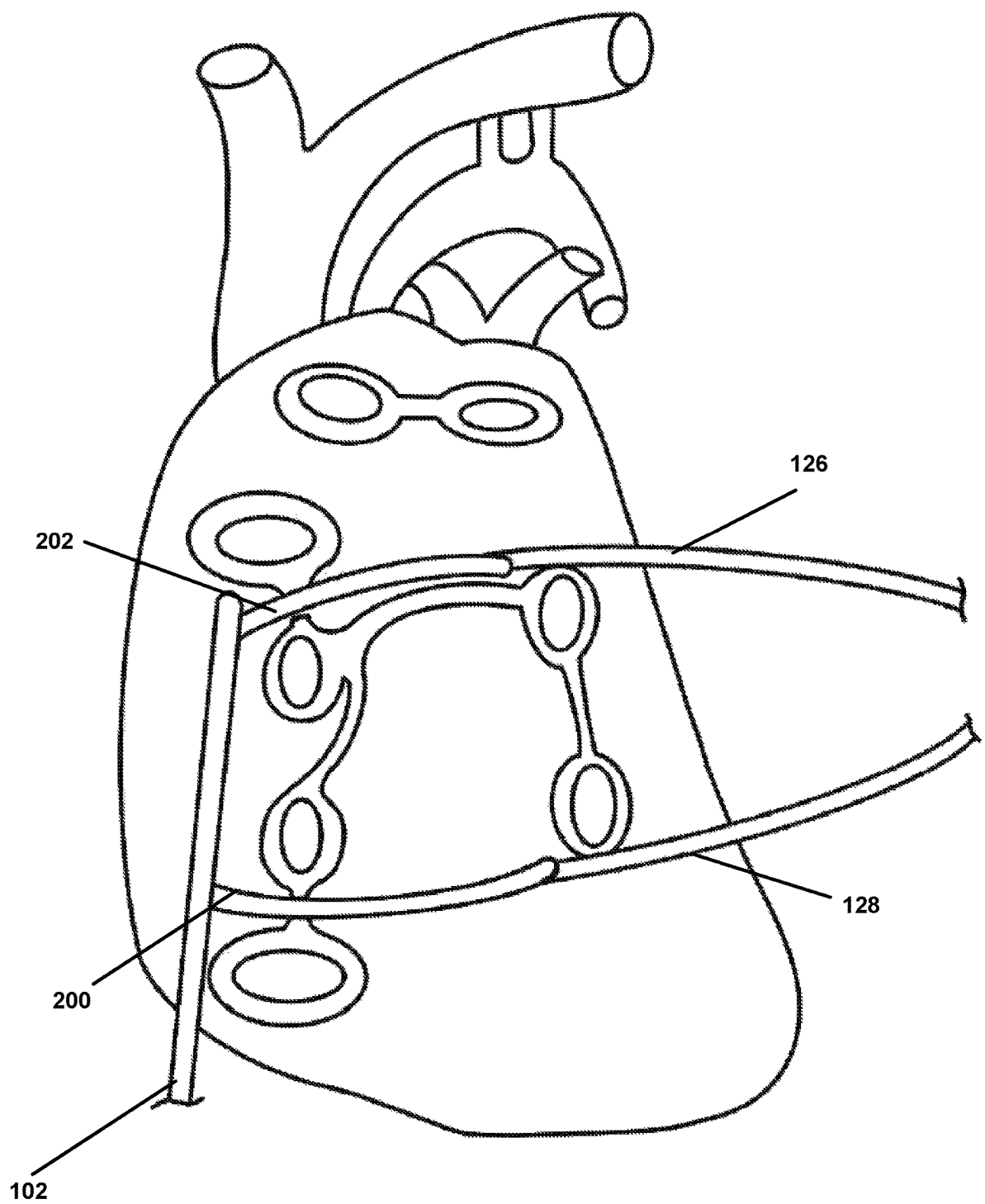
FIG. 1D illustrates an anterior view of the heart with a right-curved clamp inserted therein.

FIG. 1D illustrates an anterior view of the heart with a first ablation device 102 inserted therein. Once first catheter 128 is reduced to an appropriate length, it can then be placed onto or grasped by a first ablation device 102. The first ablation device 102 can be configured to secure the open end of the first catheter 128 via a clamp having a proximal jaw 200 and a distal jaw 202. The first ablation device 102 can be an isolator synergy clamp with right curved jaws (e.g., an "EMR" by AtriCure®). The first ablation device 102 can be introduced via the base of the inferior vena cava. Once the distal jaw 202 is attached to the first flexible guiding device 126 (e.g., via a snap-on fitting), the first flexible guiding device 126 can stay attached to the distal jaw. The proximal jaw 200 can be attached to the first catheter 128. The first catheter 128 can eventually be detached from the proximal jaw 200 so that the ablation target can be seen by the operator and reached by the first ablation device 102.

The operator can be located on the left side of the table and can apply gentle and even traction to the first flexible guiding device 126 and the catheter 128 to remove any slack from the catheter 128 and the first ablation device 102. While the operator is applying gentle traction to the first flexible guiding device 126 and the catheter 128, another operator can slowly advance the first ablation device 102 in a rotating counter-clockwise motion. The distal jaw 202 of the first ablation device 102 can then be advanced across the transverse sinus 116 while simultaneously guiding the proximal jaw 200 approximately across the floor of the oblique sinus 122.

Figure 1E:
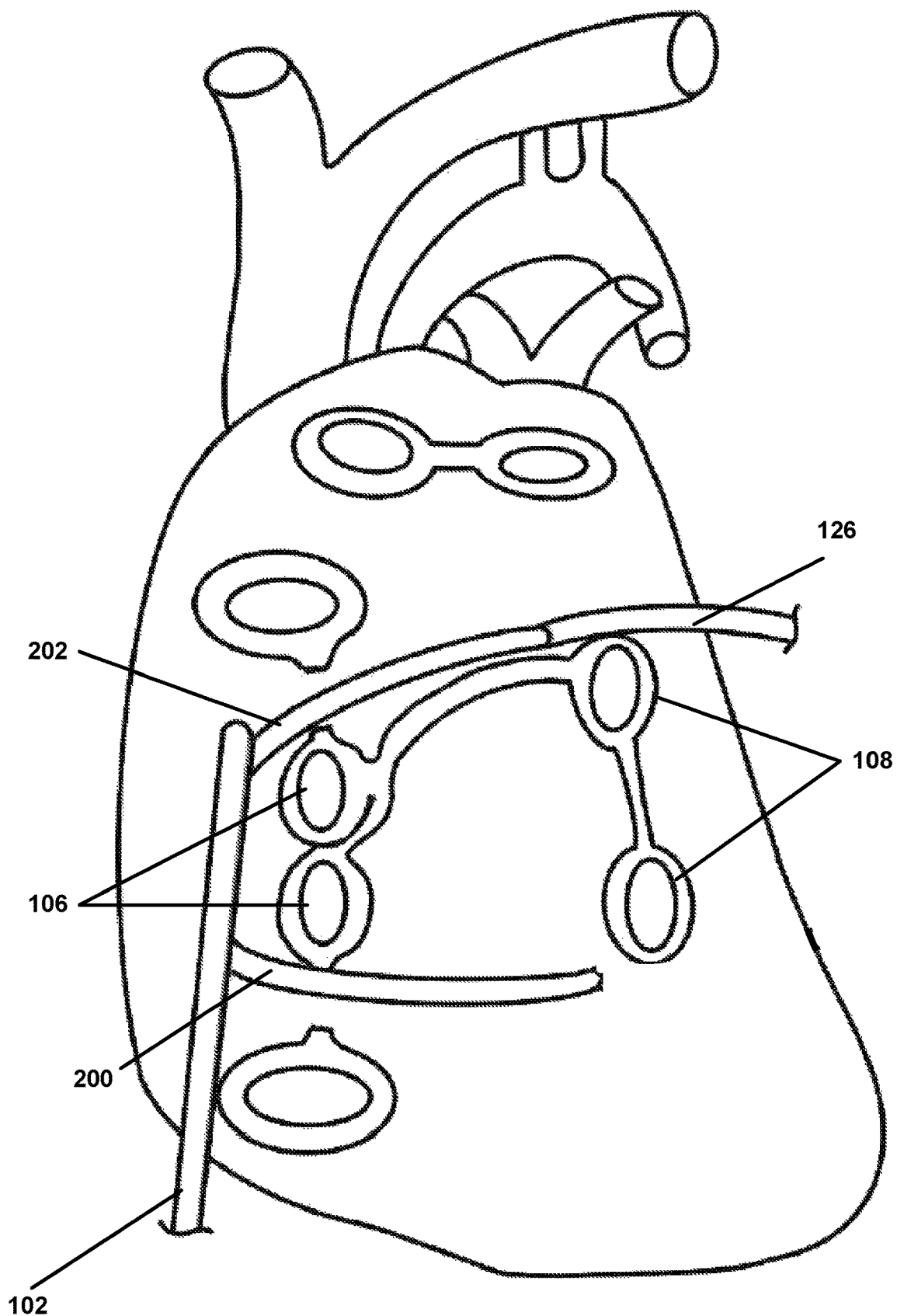
FIG. 1E illustrates an anterior view of the heart with right pulmonary veins compressed.

FIG. 1E illustrates an anterior view of the heart with right pulmonary veins 106 clamped together. After clamping, the right pulmonary veins 106 can be compressed and the tissue can be relatively flat such that no blood can get through. The posterior reflection between the superior and inferior right pulmonary veins 106 can still be intact during clamping. The surgeon can be careful only to advance jaws 200 and 202 medial of the left pulmonary veins 108 as to not clamp all of the right pulmonary veins 106 and the left pulmonary veins 108 at the same time.

The first ablation device 102 can be advanced until the proximal jaw 200 reaches the inferomedial aspect or the left inferior pulmonary vein. In some variations, this can be accomplished by orienting the shaft of the first ablation device 102 toward the right and caudal aspect of a sternotomy. To ensure that the atrial tissue between the jaws is at a level that can ensure the quality of ablation, the proximal jaw 200 can be advanced no further than the inferomedial aspect of the left inferior pulmonary vein. For best visualization, the ventricle can be retracted in standard fashion with a sponge. The method can further comprise opening and extracting the first ablation device 102 while the catheter and the first flexible guiding device 126 are maintained proximal to the transverse sinus 116. The first catheter 128 can be removed from within the oblique sinus 122. Once catheter 128 is removed, the proximal and distal jaws of the first ablation device 102 can be closed medial to the left pulmonary veins 108 to perform ablation.

Figure 1F:
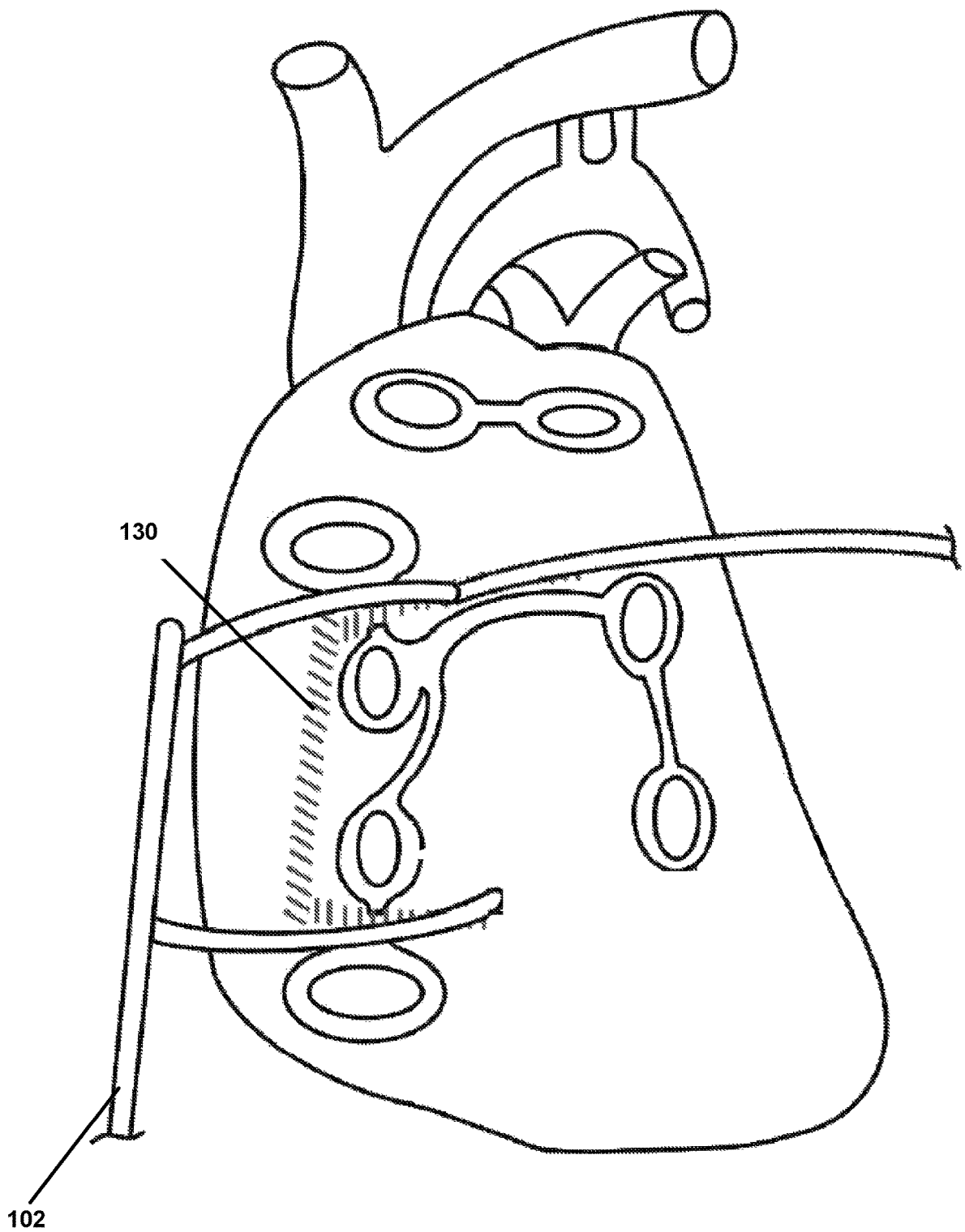
FIG. 1F illustrates an anterior view of the heart with ablation lines thereon.

FIG. 1F illustrates an anterior view of the heart with first ablation lines 130 thereon. The ablation can then be performed with standard techniques using the first ablation device 102. After performing ablation, the user can open and retract the first ablation device 102. The first ablation device 102 can then be removed from the chest while maintaining the first flexible guiding device 126 within the transverse sinus 116.

The atrium can be marked, such as by using a methylene blue pen, to eventually ensure that ablation lines properly overlap. A long tonsil can be used to hold the tip of the pen to give a proper angle to avoid tensioning the first ablation device 102 and to decrease undesired lifting the heart.

Figure 1G:
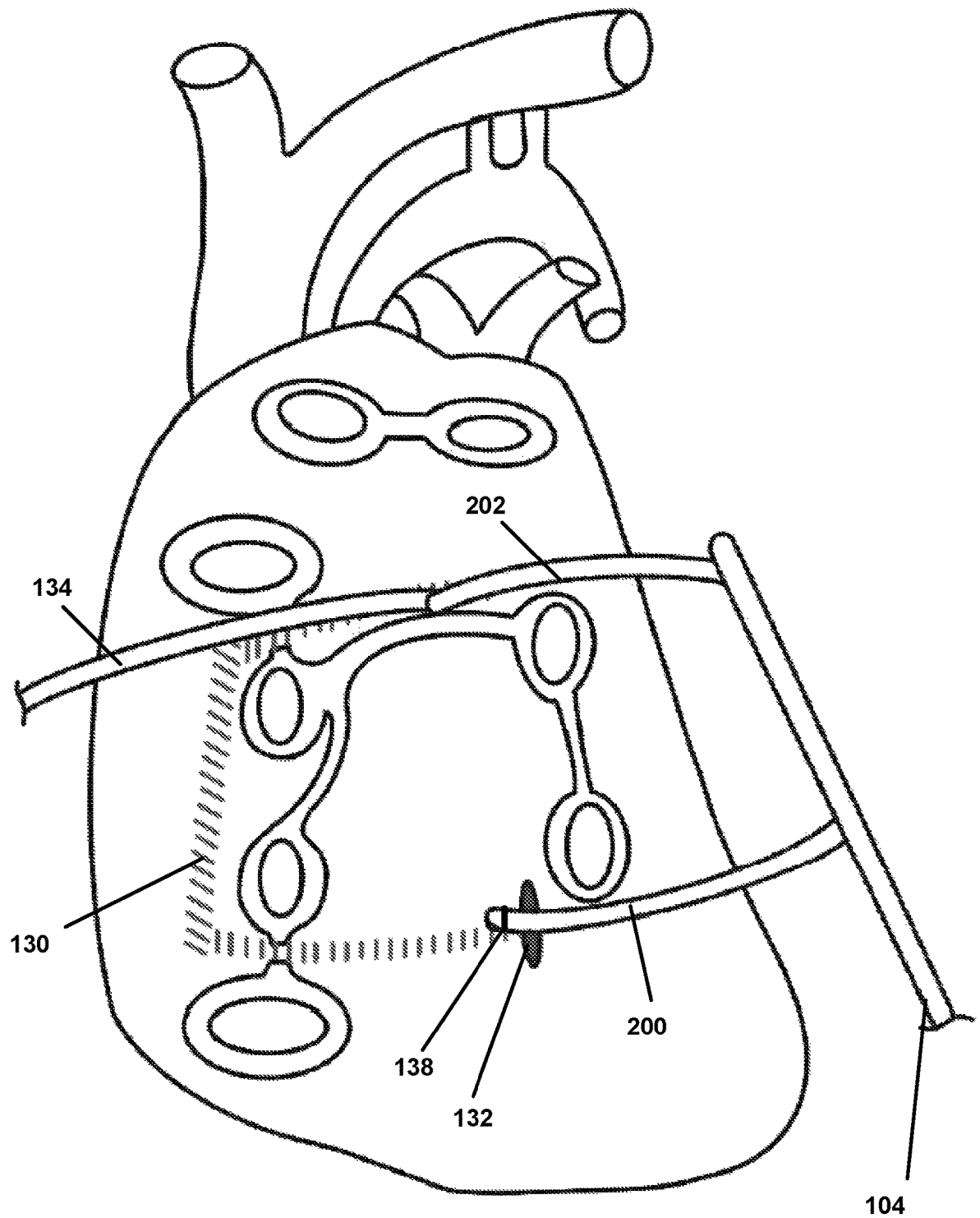
FIGS. 1G and 1H illustrate an anterior view of the heart with a left-curved clamp inserted therein and advanced past a marked target on the heart.
Figure 1H:
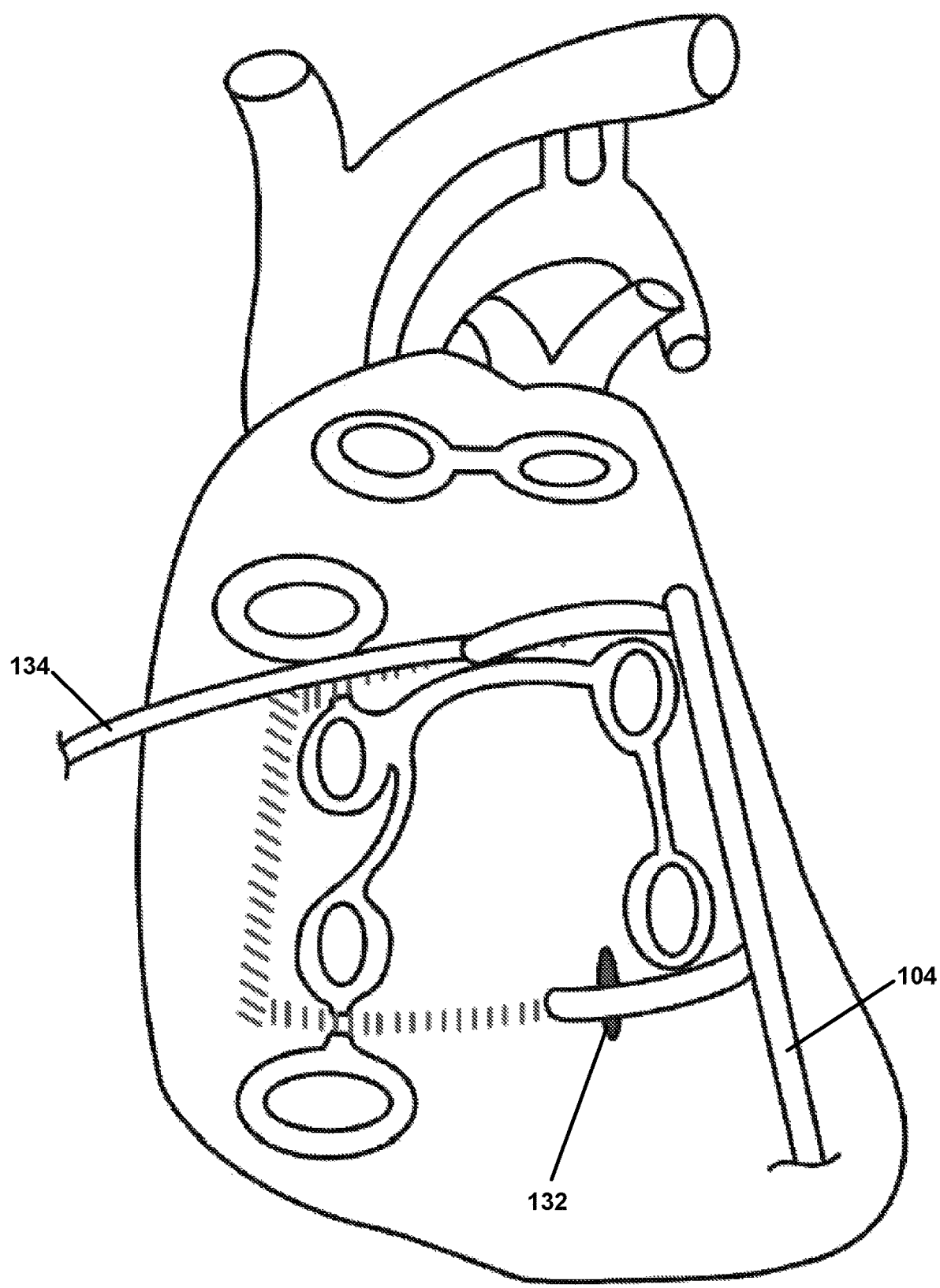

FIGS. 1G and 1H illustrate an anterior view of the heart with a left-curved clamp inserted therein and advanced past a marked target on the heart. Once the first ablation is performed, a second flexible guiding device 134 can be introduced and placed on the sterile field for use. The method can further comprise connecting a distal end of the second flexible guiding device 134 to a distal end of the first flexible guiding device 126 and subsequently retracting the first flexible guiding device 126. A distal jaw 202 of a second ablation device 104 (e.g., an "EML" by AtriCure®). can be attached to the second flexible guiding device 134. Since the right side of the heart can comprise a vessel to go through (i.e., the location between the right inferior pulmonary vein and the inferior vena cava) and the left side of the heart does not, there can be no need for a second catheter when introducing a second ablation device 104

A distal end of the first flexible guiding device 126 can be tied or sutured to a distal tip of the second flexible guiding device 134. Applying gentle traction, the operator can retract the first flexible guiding device 126 back through the transverse sinus 116. In doing so, this can thereby pull the second flexible guiding device 134 out completely through the transverse sinus 116 and beyond the superior vena cava 112. Once retracted, the first flexible guiding device 126 can be unattached (e.g., cut) from the second flexible guiding device 134.

The second flexible guiding device 134 can correspond to a second ablation device 104 such as a bipolar RF energy device as described above for use in ablation procedures. After or concurrent to the movement of the first flexible guiding device 126 and the second flexible guiding device 134, the second ablation device 104 (e.g., an isolator synergy clamp with left curved jaws) can be opened and the second flexible guiding device 134 can be attached thereto. The ventricle can then be retracted with another sponge. Control of the left atrial appendage can also be obtained in standard fashion with the sponge. The method can further comprise attaching the second flexible guiding device 134 to a second ablation device 104 after detaching the first flexible guiding device 126 from the second flexible guiding device 134.

While an operator applies gentle tension and/or traction to the second flexible guiding device 134 from the right side of the table, another operator can slowly advance the second ablation device 104, carefully guiding the distal jaw 202 across the transverse sinus while approximately simultaneously guiding the proximal jaw 200 across the floor of the oblique sinus 122. This maneuver can be performed while the left ventricle is being retracted so that the proximal jaw 200 of the second ablation device 104 can be clearly visualized at all times.

The second ablation device 104 can be gently positioned into place so that the proximal jaw 200 of the second ablation device 104 clearly crosses the marked position on the atrium placed prior to the first ablation (e.g., the methylene blue mark 132 placed prior to the first ablation). This can be accomplished by orienting a shaft of the second ablation device 104 of the towards a left lateral position. The second ablation device 104 can be advanced into place with a clockwise rotation followed by a downward/posterior advancement of the proximal and distal jaws 200, 202 of the second ablation device 104.

Prior to closing the second ablation device 104, the operator can ensure that the LAA is not within the jaws 200, 202 of the device and the second ablation device 104 is positioned lateral to the base and away from the circumflex artery. Additionally, the operator can ensure that the second ablation device 104 is positioned so that once closed, a perpendicular black line 138 at the distal tip of the second ablation device 104 proximal jaw is beyond the methylene blue mark 132 to ensure that the first ablation lines 130 and the second ablation lines 136 (seen in FIG. 1J) completely cross, leaving no gaps in the ablation lines. As such, blue mark 132 can be made on the medial side of the left pulmonary veins 108. The operator can advance the jaws only as far as the proximal jaw 200 needs to cross the previous first ablation line, indicated by blue mark 132. The second ablation device 104 can then be closed and the ablation can be performed per standard techniques.

Figure 1I:
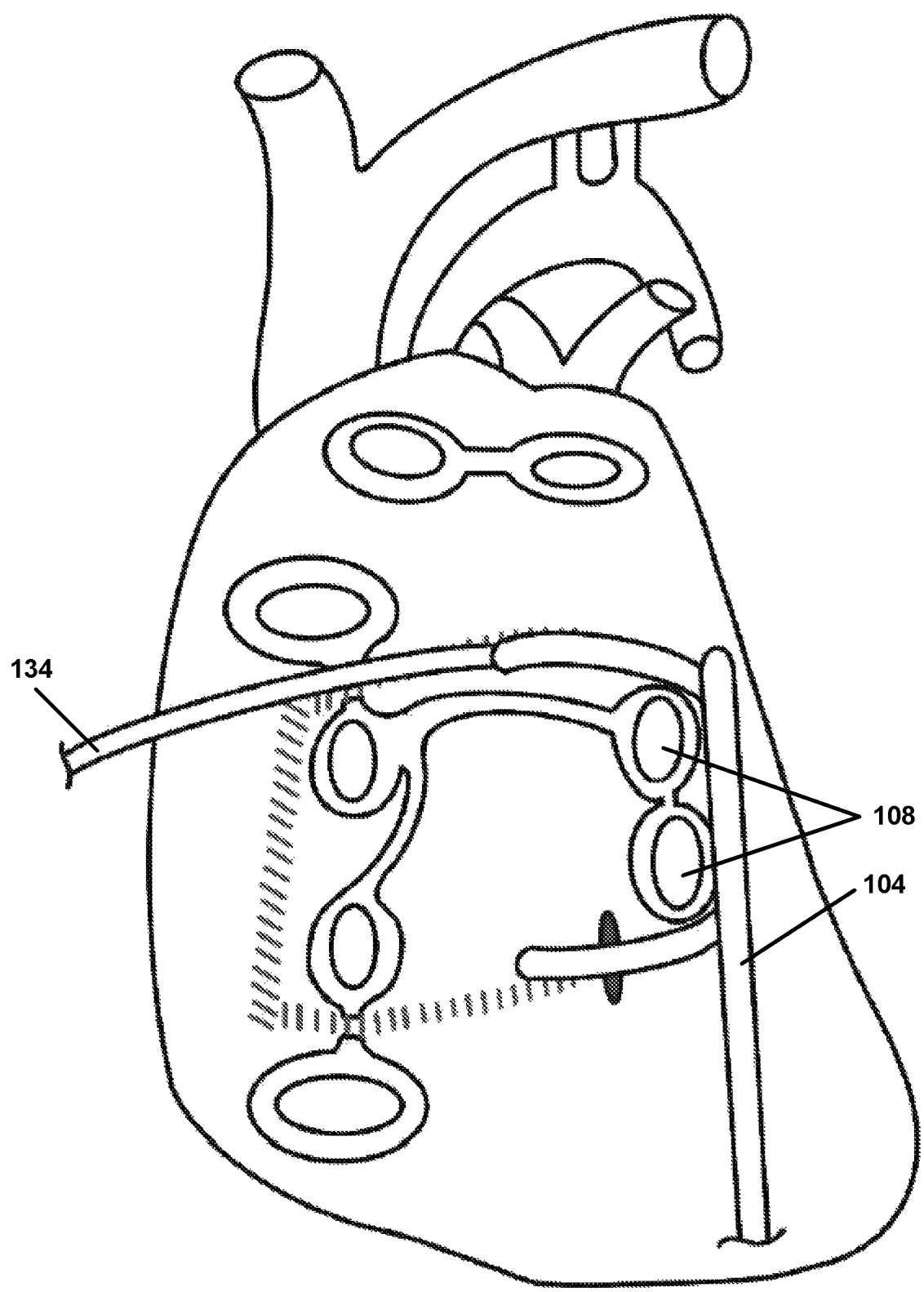
FIG. 1I illustrates an anterior view of the heart with left pulmonary veins compressed.

FIG. 1I illustrates an anterior view of the heart with left pulmonary veins clamped together. The proximal and distal jaws 200 and 202 can clamp medial to the veins and ablation is performed once the left pulmonary veins 108 are compressed and the tissue can be relatively flat such that no blood should get through.

The method can further comprise opening and extracting the second ablation device 104 in response to an ablation line from the first ablation device 102 crossing an ablation line from the second ablation device. After performing the second ablation, the jaws of the second ablation device 104 can be opened to release the tissue within.

Figure 1J:
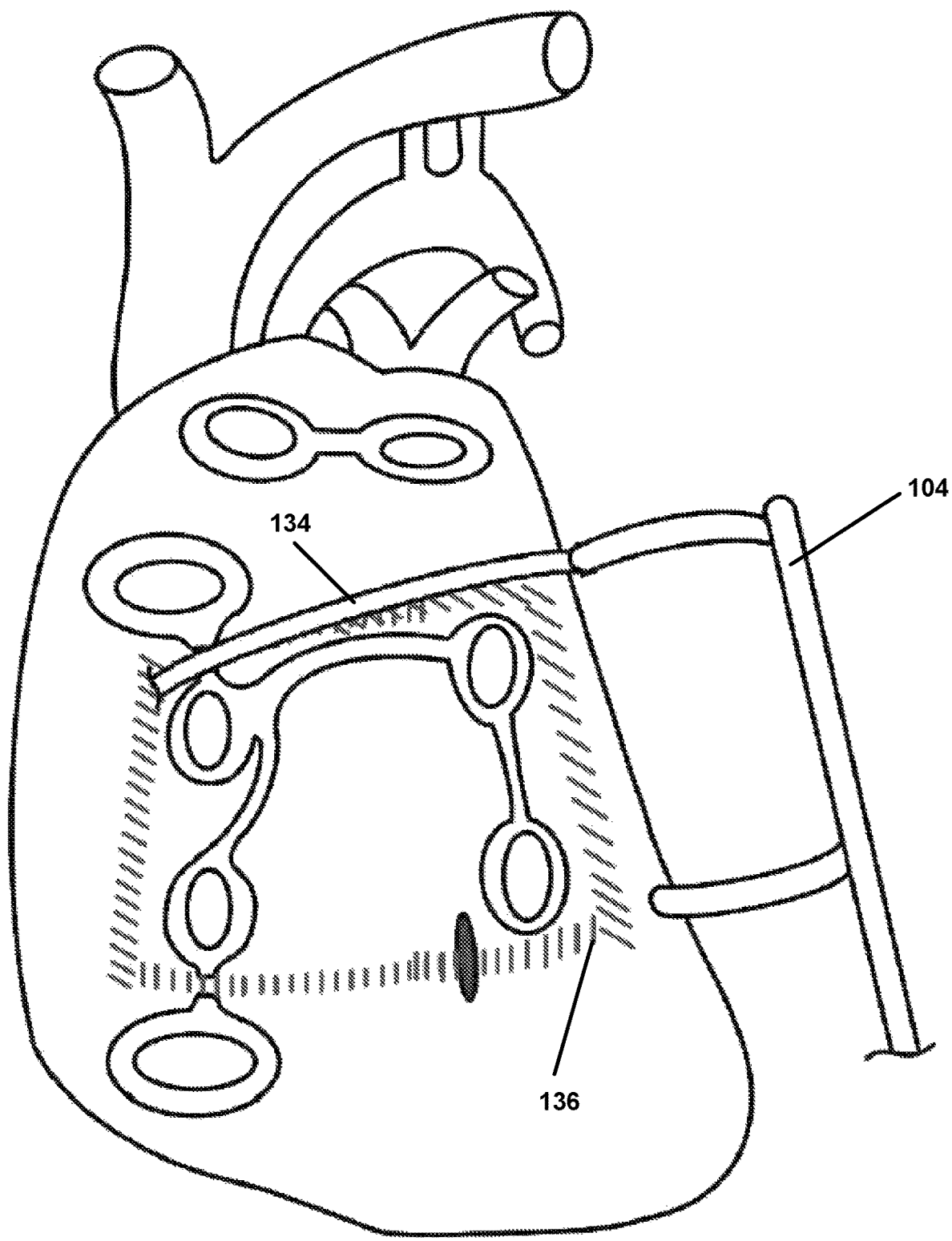
FIG. 1J illustrates an anterior view of the heart with the left-curved clamp being withdrawn from the heart after ablation.
Figure 1K:
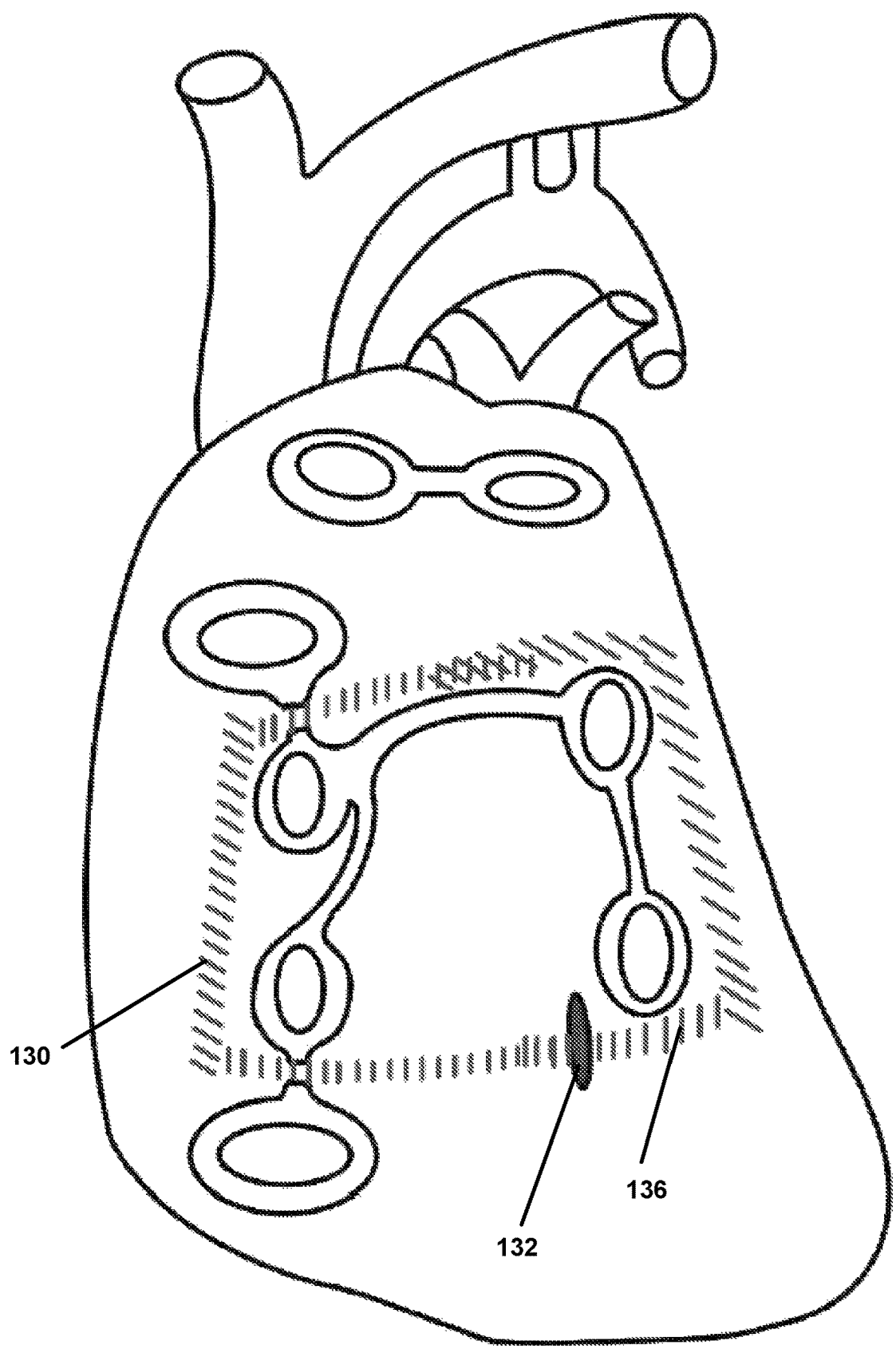
FIG. 1K illustrates an anterior view of the heart with a complete ablation circle around the pulmonary veins.

FIG. 1J illustrates an anterior view of the heart with the left-curved clamp being withdrawn from the heart after ablation. As a result, the first ablation lines 130 and the second ablation lines 136 can form a box or circle around the four pulmonary veins (two right pulmonary veins 106 and two left pulmonary veins 108) as additionally seen in FIG. 1K. The operator can then make sure that the ablation lines are all connected such that there are no gaps in the box or circle. FIG. 1K illustrates an anterior view of the heart with a complete ablation circle around the pulmonary veins.

The method can further comprise repeating operations related to the second ablation device in response to the ablation line from the first ablation device 102 not crossing the ablation line from the second ablation device 104. If gaps are found, or areas found where the ablation lines do not cross, the second ablation device 104 can be reintroduced as described above and the ablation can be performed again.

FIG. 2A illustrates an example of a clamping device for use with the methods descried herein. This device can be used to create lesions on the heart to treat atrial fibrillation. It should be understood that the jaws 200 and 202 can be provided with curves towards the right or the left orientation. The ablation device 102 or 104 can include a shaft 210, a distal jaw 202, a proximal jaw 200, and a handle 208. As shown here, the shaft 210 can be straight and rigid; however, it can also be one or more of the following: curved, flexible, malleable, and articulated. In the present exemplary embodiment, the jaws 200, 202 can each have slender electrodes 206 on the clamping surfaces to effect tissue ablation through bi-polar or mono-polar RF energy, for example. The jaws 200, 202 can be curved; however, the jaws could also be straight or curved in other configurations. As shown here, the jaws 200, 202 can be in an opened position where the jaws are separated and substantially parallel to one another. The jaws both extend laterally relative the shaft 210, but not necessarily normal the shaft. The proximal jaw 200 can be longitudinally repositioned relative to the shaft 210 independent of the distal jaw 202. In this example, the distal jaw 202 can be fixed in position relative the shaft 210. Preferably, in this exemplary embodiment, the proximal jaw 200 can lock in position parallel to the distal jaw 202 when the jaws are adjacent and in the closed position or while the proximal jaw 200 is being moved toward the closed position. Those skilled in the art will understand that the articulated ablation device 102 or 104 is an exemplary embodiment and does not operate to limit the claims, nor any aspects of the other exemplary embodiments disclosed herein.

Alternatively, however, the distal jaw 202 can be repositionable to move longitudinally along the shaft 210 to a closed position where the jaws 200, 202 are adjacent and substantially parallel to one another. Preferably, in this alternate exemplary embodiment, the distal jaw 202 can lock in position parallel to the proximal jaw 200 when the jaws are adjacent and in the closed position or while the distal jaw 202 is being moved toward the proximal jaw 200.

In one exemplary variation, the distal jaw 202 can be articulated (e.g., pivoted) and is "limp" when articulating. Accordingly, in such a circumstance, the distal jaw 202 can articulate passively in response to minimal external forces. Optionally, the tip of the distal jaw 202 includes a fastener 204 which can be to interface with a male fastener counterpart of an instrument guide (not shown). For instance, the instrument guide can be an elongate flexible member. When the instrument guide is anchored to the fastener 204, the distal jaw 202 can be positioned to a desired location in the surgical field by pulling the instrument guide. Preferably, the distal jaw 202 can be in its articulated "limp" position so as to reduce interference with surrounding or adjacent anatomical features. The distal and proximal jaws can then be adjusted so that the tissue being treated is interposed between the jaws 200, 202. The jaws can then be closed and the tissue ablated. After treatment is concluded, and the clamp is opened, the distal jaw 202 will return to its articulated "limp" position, thereby repositioning the instrument guide from the surgical area.

The electrodes 206 can extend along each mating surface of each jaw 200, 202. The electrodes 206 can be adapted to be connected to an RF energy source such that, when activated, the electrodes 206 can be of opposite polarity. In an embodiment, the electrodes 206 can be made of gold-plated copper and can have a length of about 3.0 cm to 8.0 cm and a width of about 0.12 mm to 0.6 mm, for example.

Examples of RF devices, instrument guides, and exemplary surgical procedures are further described in U.S. Pat. Nos. 7,001,415, 8,029,528, and 10,398,495, which are hereby incorporated by reference in their entirety as if fully set forth below in its entirety and for all applicable purposes.

FIG. 2B illustrates an example of a flexible guiding device 126 to be used in accordance with the methods described herein. The flexible guiding device 126 can have a snap attachment tip 212 for attachment with fastener 204 of ablation device 102. The snap attachment tip 212 can be inserted into the fastener 204 of the distal jaw 202. Elastic portion 214 of flexible guiding device 126 can be made with any suitable elastic material. The elastic portion 214 can be sufficiently stretched to be pulled and configured to position around tissue structures. When flexible guiding devices 126, 134 are connected to respective ablation devices 102, 104, the elasticity of the elastic portion 214 can help position the jaws of the ablation devices to a desired position.

Figure 3A:
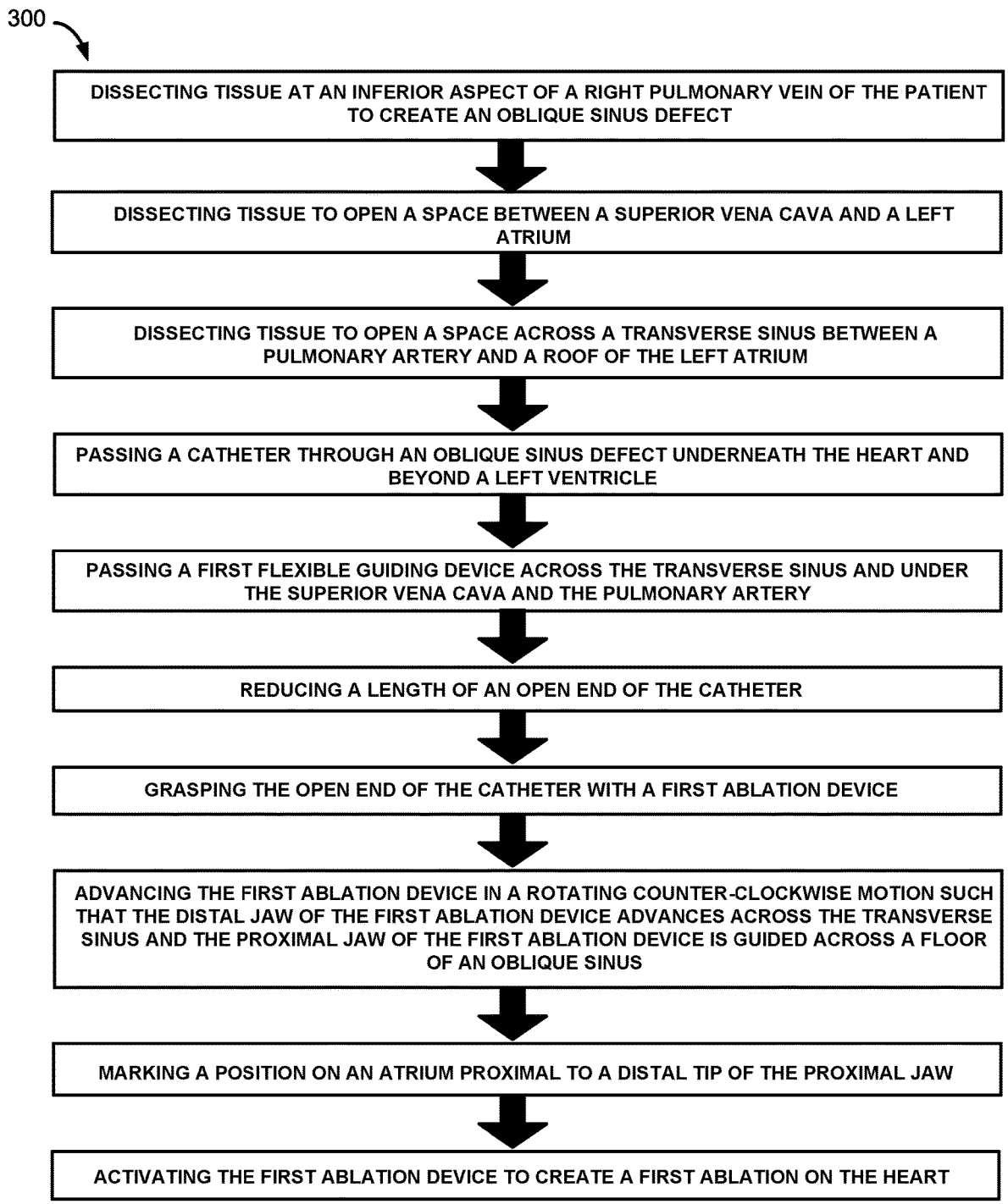
FIGS. 3A and 3B illustrate flow charts of variations of methods of treating a heart of a patient having a cardiac arrhythmia.

As generally seen in FIG. 3A, a method of treating a heart of a patient having a cardiac arrhythmia is disclosed. The method can comprise dissecting tissue at an inferior aspect of a right inferior pulmonary vein of the patient to create an oblique sinus defect, dissecting tissue to open a space between a superior vena cava and a left atrium, and dissecting tissue to open a space across a transverse sinus between a pulmonary artery and a roof of the left atrium. The method can further comprise passing a catheter through an oblique sinus defect underneath the heart and beyond a left ventricle and passing a first flexible guiding device across the transverse sinus and under the superior vena cava and the pulmonary artery.

The method can further comprise reducing a length of an open end of the catheter and grasping the open end of the catheter with a first ablation device. Reducing the length of the open end of the catheter can comprise reducing the length by about 50% and can comprise cutting the open end of the catheter. The first ablation device can comprise a proximal jaw and a distal jaw configured to secure the open end. The method can further comprise advancing the first ablation device in a rotating counter-clockwise motion such that the distal jaw of the first ablation device advances across the transverse sinus and the proximal jaw of the first ablation device is guided across a floor of an oblique sinus. The method can further comprise marking a position on an atrium proximal to a distal tip of the proximal jaw and activating the first ablation device to create a first ablation on the heart.

The method can further comprise placing the open end of the catheter onto the proximal jaw of the first ablation device. The method can further comprise removing slack from the catheter and the first ablation device. The method can further comprise advancing the first ablation device until the proximal jaw reaches up to the left inferior pulmonary vein. The method can further comprise closing the proximal and distal jaws of the first ablation device. The method can further comprise creating a marked position on the atrium proximal to a distal tip of the proximal jaw. The method can further comprise opening and extracting the first ablation device while the catheter and the first flexible guiding device are maintained proximal to the transverse sinus.

Figure 3B:
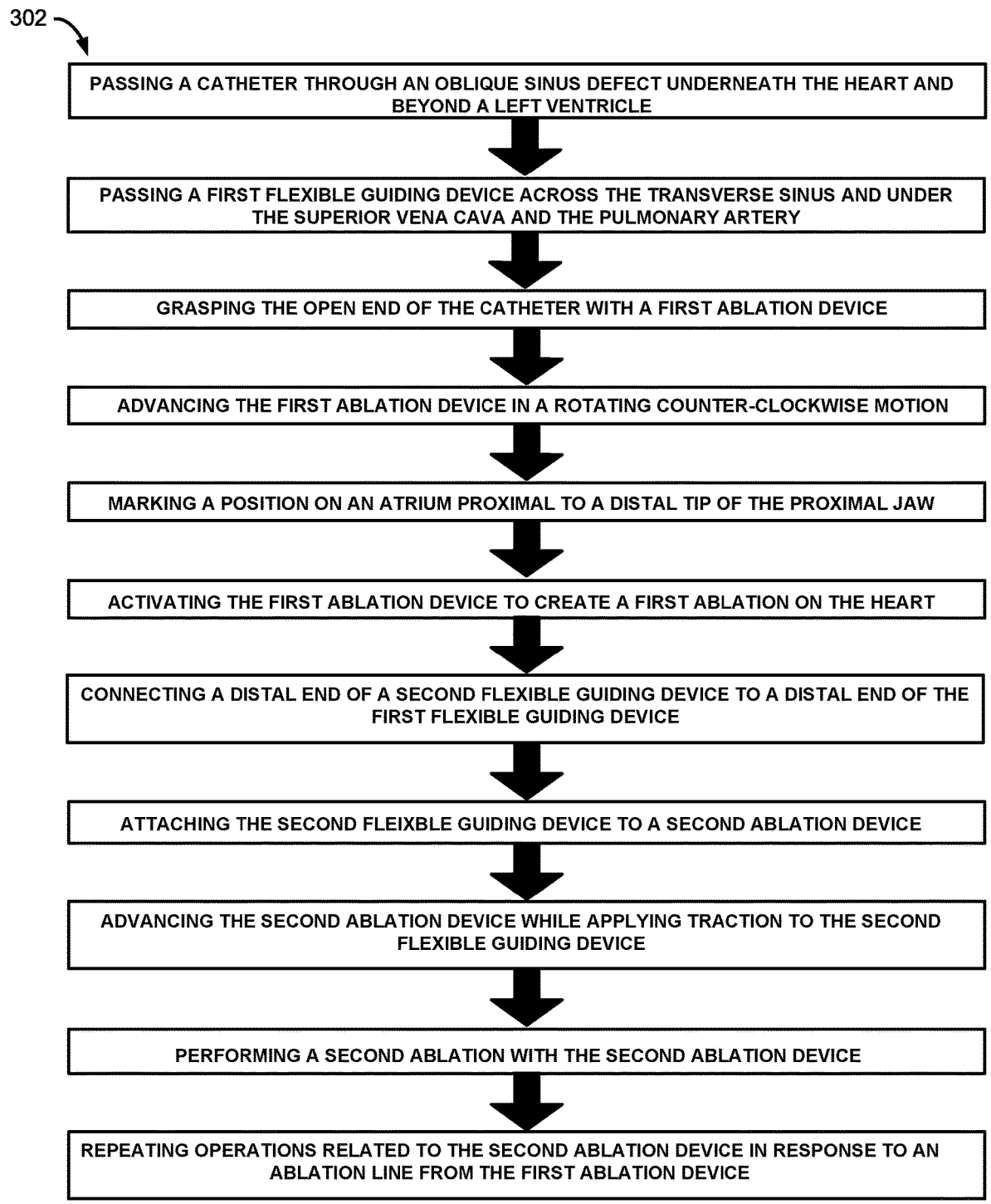

Additionally, as generally seen in FIG. 3B, the method can further comprise connecting a distal end of a second flexible guiding device to a distal end of the first flexible guiding device and retracting the first flexible guiding device. Retracting the first flexible guiding device can cause the second flexible guiding device to be pulled through the transverse sinus and beyond the superior vena cava. The method can further comprise detaching the first flexible guiding device from the second flexible guiding device. The method can further comprise attaching the second flexible guiding device to a second ablation device after detaching the first flexible guiding device from the second flexible guiding device. The method can further comprise advancing the second ablation device while applying traction to the second flexible guiding device such that a distal jaw of the second ablation device extends across the transverse sinus until a proximal jaw of the second ablation device crosses the marked position on the atrium. Advancing the second ablation device can comprise a clockwise rotation and a downward advancement of the proximal and distal jaws of the second ablation device.

A second ablation can be performed with the second ablation device. The method can further comprise opening and extracting the second ablation device in response to an ablation line from the first ablation device crossing an ablation line from the second ablation device. The method can further comprise repeating operations related to the second ablation device in response to the ablation line from the first ablation device not crossing the ablation line from the second ablation device. The first ablation device can be advanced no further than an inferomedial aspect of a left inferior pulmonary vein. The method can further comprise retracting the left ventricle with a sponge.

While the exemplary embodiments have been described in some detail, by way of example and for clarity of understanding, those of skill in the art will recognize that a variety of modification, adaptations, and changes can be employed. Hence, the scope of the present invention should be limited solely by the claims.

What is claimed is:

1. A method of treating a heart of a patient having a cardiac arrhythmia, the method comprising:
    dissecting tissue at an inferior aspect of a right inferior pulmonary vein of the patient to create an oblique sinus defect;
    dissecting tissue to open a space between a superior vena cava and a left atrium;
    dissecting tissue to open a space across a transverse sinus between a pulmonary artery and a roof of the left atrium;
    passing a catheter through an oblique sinus defect underneath the heart and beyond a left ventricle;
    passing a first flexible guiding device across the transverse sinus and under the superior vena cava and the pulmonary artery;
    reducing a length of an open end of the catheter;
    grasping the open end of the catheter with a first ablation device, wherein the first ablation device comprises a proximal jaw and a distal jaw configured to secure the open end;
    advancing the first ablation device in a rotating counter-clockwise motion such that the distal jaw of the first ablation device advances across the transverse sinus and the proximal jaw of the first ablation device is guided across a floor of an oblique sinus;
    marking a position on an atrium proximal to a distal tip of the proximal jaw prior to any ablation;
    activating the first ablation device to create a first ablation on the heart, wherein the first ablation overlaps the marked position;
    connecting a distal end of a second flexible guiding device to a distal end of the first flexible guiding device;
    detaching the first flexible guiding device from the second flexible guiding device;
    attaching the second flexible guiding device to a second ablation device after detaching the first flexible guiding device from the second flexible guiding device; and
    performing a second ablation with the second ablation device, wherein the second ablation overlaps the marked position.

2. The method of claim 1, wherein reducing the length of the open end of the catheter further comprises placing the open end of the catheter onto the proximal jaw of the first ablation device.

3. The method of claim 1, further comprising removing slack from the catheter and the first flexible guiding device.

4. The method of claim 1, wherein advancing the first ablation device in the rotating counter-clockwise motion further comprises advancing the first ablation device until the proximal jaw reaches up to a left inferior pulmonary vein.

5. The method of claim 1, further comprising closing the proximal and distal jaws of the first ablation device.

6. The method of claim 1, further comprising opening and extracting the first ablation device while the catheter and the first flexible guiding device are maintained proximal to the transverse sinus.

7. The method of claim 1, further comprising advancing the second ablation device while applying traction to the second flexible guiding device such that a distal jaw of the second ablation device extends across the transverse sinus until a proximal jaw of the second ablation device crosses the marked position on the atrium.

8. The method of claim 7, wherein advancing the second ablation device comprises a clockwise rotation and a downward advancement of the proximal and distal jaws of the second ablation device.

9. The method of claim 1, further comprising opening and extracting the second ablation device in response to an ablation line formed by the first ablation from the first ablation device crossing an ablation line formed by the second ablation from the second ablation device.

10. The method of claim 9, further comprising performing further ablations by the second ablation device in response to the ablation line from the first ablation device not crossing the ablation line from the second ablation device.

11. The method of claim 1, wherein the first ablation device is advanced no further than an inferomedial aspect of a left inferior pulmonary vein.

12. The method of claim 1, further comprising retracting the left ventricle with a sponge.

13. The method of claim 1, wherein reducing the length of the open end of the catheter comprises reducing the length by about 50%.

14. A method of treating a heart of a patient having a cardiac arrhythmia, the method comprising:
    passing a catheter through an oblique sinus defect underneath the heart and beyond a left ventricle;

passing a first flexible guiding device across a transverse sinus and under a superior vena cava and a pulmonary artery;

grasping an open end of the catheter with a first ablation device, wherein the first ablation device comprises a proximal jaw and a distal jaw configured to secure the open end;

advancing the first ablation device in a rotating counter-clockwise motion such that the distal jaw of the first ablation device advances across the transverse sinus and the proximal jaw of the first ablation device is guided across a floor of an oblique sinus;

marking a position on an atrium proximal to a distal tip of the proximal jaw prior to any ablation;

activating the first ablation device to create a first ablation on the heart, wherein the first ablation overlaps the marked position;

connecting a distal end of a second flexible guiding device to a distal end of the first flexible guiding device;

retracting the first flexible guiding device such that the second flexible guiding device is pulled through the transverse sinus and beyond the superior vena cava;

detaching the first flexible guiding device from the second flexible guiding device;

attaching the second flexible guiding device to a second ablation device;

advancing the second ablation device while applying traction to the second flexible guiding device such that a distal jaw of the second ablation device extends across the transverse sinus until a proximal jaw of the second ablation device crosses the marked position on the atrium, wherein advancing the second ablation device comprises a clockwise rotation and a downward advancement of the proximal and distal jaws of the second ablation device;

performing a second ablation with the second ablation device, wherein the second ablation overlaps the marked position; and performing further ablations by the second ablation device in response to an ablation line formed by the first ablation from the first ablation device.

15. A method of treating a heart of a patient having a cardiac arrhythmia, the method comprising:

dissecting tissue at an inferior aspect of a right inferior pulmonary vein of the patient to create an oblique sinus defect;

passing a catheter through the oblique sinus defect underneath the heart and beyond a left ventricle;

passing a first flexible guiding device across a transverse sinus and under a superior vena cava and a pulmonary artery;

cutting an open end of the catheter;

grasping the open end of the catheter with a first ablation device, wherein the first ablation device comprises a proximal jaw and a distal jaw configured to secure the open end;

advancing the first ablation device in a rotating counter-clockwise motion such that the distal jaw of the first ablation device advances across the transverse sinus and the proximal jaw of the first ablation device is guided across a floor of an oblique sinus;

marking a position on an atrium proximal to a distal tip of the proximal jaw prior to any ablation;

activating the first ablation device to create a first ablation on the heart, wherein the first ablation overlaps the marked position;

connecting a distal end of a second flexible guiding device to a distal end of the first flexible guiding device;

retracting the first flexible guiding device such that the second flexible guiding device is pulled through the transverse sinus and beyond the superior vena cava;

detaching the first flexible guiding device from the second flexible guiding device;

attaching the second flexible guiding device to a second ablation device;

advancing the second ablation device while applying traction to the second flexible guiding device such that a distal jaw of the second ablation device extends across the transverse sinus until a proximal jaw of the second ablation device crosses the marked position on the atrium, wherein advancing the second ablation device comprises a clockwise rotation and a downward advancement of the proximal and distal jaws of the second ablation device;

performing a second ablation with the second ablation device, wherein the second ablation overlaps the marked position; and performing further ablations by the second ablation device in response to an ablation line formed by the first ablation from the first ablation device.

* * * * *